(12) United States Patent
Kumar et al.

(10) Patent No.: US 11,773,413 B2
(45) Date of Patent: Oct. 3, 2023

(54) BOOSTER COMPOSITION TO IMPROVE BIOGAS YIELD AND TO STABILIZE THE DIGESTER PERFORMANCE

(71) Applicant: Indian Oil Corporation Limited, Mumbai (IN)

(72) Inventors: Manoj Kumar, Faridabad (IN); Srikanth Sandipam, Faridabad (IN); Prakash Chandra Sahoo, Faridabad (IN); Ravi Prakash Gupta, Faridabad (IN); Suresh Kumar Puri, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 4 days.

(21) Appl. No.: 17/367,897

(22) Filed: Jul. 6, 2021

(65) Prior Publication Data
US 2022/0002761 A1    Jan. 6, 2022

(30) Foreign Application Priority Data
Jul. 6, 2020   (IN) .............................. 202021028639

(51) Int. Cl.
*C12P 5/02*     (2006.01)
*C02F 11/04*    (2006.01)

(52) U.S. Cl.
CPC .............. *C12P 5/023* (2013.01); *C02F 11/04* (2013.01); *C02F 2305/06* (2013.01); *C02F 2305/08* (2013.01)

(58) Field of Classification Search
CPC ...... C12P 5/023; C02F 11/04; C02F 2305/06; C02F 2305/08
See application file for complete search history.

(56) References Cited

U.S. PATENT DOCUMENTS

| | | | | |
|---|---|---|---|---|
| 5,342,524 A | * | 8/1994 | Gaddy | ...................... C02F 3/34 435/801 |
| 2012/0021476 A1 | * | 1/2012 | Friedmann | .............. C12P 5/023 435/167 |

FOREIGN PATENT DOCUMENTS

| EP | 2592055 A1 | 5/2013 |
|---|---|---|
| EP | 2683662 B1 | 11/2017 |

(Continued)

OTHER PUBLICATIONS

Paritosh Kunwar et al, "Additives as a Support Structure for Specific Biochemical Activity Boosts in Anaerobic Digestion: A Review", Frontiers in Energy Research, (Jun. 11, 2020), vol. 8;pp. 1-17 (Year: 2020).*

(Continued)

*Primary Examiner* — Latosha Hines
(74) *Attorney, Agent, or Firm* — Workman Nydegger (57) ABSTRACT

The present invention relates to a booster composition for enhancing the biogas yield and stabilizing the operation of a biomethanation plant, a method for the preparation of said booster composition and a method for enhancing the biogas yield and stabilizing the operation of a biomethanation plant using said composition by ameliorating the effect of shock conditions like pH and temperature. The booster composition comprises of specifically defined constituents selected from controlled release agents, redox potential balancers, direct interspecies electron transfer (DIET) improvers, micronutrient balancers, and Co-factors.

18 Claims, 5 Drawing Sheets

(56) References Cited

FOREIGN PATENT DOCUMENTS

| PL | 421577 A1 | 11/2018 | |
|---|---|---|---|
| PL | 236962 B1 | 3/2021 | |
| WO | WO-2014094053 A1 * | 6/2014 | ............. C09K 8/582 |
| WO | WO2014094053 A1 | 6/2014 | |

OTHER PUBLICATIONS

Paritosh Kunwar et al, "Additives as a Support Structure for Specific Biochemical Activity Boosts in Anaerobic Digestion: A Review", Frontiers in Energy Research, (Jun. 11, 2020), vol. 8, doi:10.3389/fenrg.2020.00088, XP055866505 [Y] 3-5 * the whole document * [A] 1,2.

Tasneem Abbasi et al, "Role of Vitamins B-3 and C in the Fashioning of Granules in UASB Reactor Sludge", Applied Biochemistry and Biotechnology, Humana Press Inc, New York, (May 2, 2012), vol. 167, No. 2, doi:10.1007/S12010-012-9691-Y, ISSN 1559-0291, pp. 348-357, XP035058383 [Y] 3-5 * abstract * [A] 1,2.

Izadi Parnian et al, "Influence of vitamin coupled with micronutrient supplement on the biomethane production, process stability, and performance of mesophilic anaerobic digestion", Biomass and Bioenergy, Amsterdam, NL, (Oct. 1, 2020), vol. 141, doi:10.1016/j.biombioe.2020.105706, ISSN 0961-9534, p. 105706, XP055866094 [AP] 1-5 * abstract *.

European Search report for EP 21182723 dated Nov. 29, 2021, 3 pages.

* cited by examiner

Fig. 7B under the dissertation field of the invention

BOOSTER COMPOSITION TO IMPROVE BIOGAS YIELD AND TO STABILIZE THE DIGESTER PERFORMANCE

FIELD OF THE INVENTION

The present invention relates to a booster composition to improve the biogas yield, stabilize biomethanation plant operation, and ameliorate the effect of shock conditions. The present invention also relates to a composition for fast recovery of microbial populations to maintain stabilized operation of the biomethanation plant.

BACKGROUND OF THE INVENTION

Biogas is produced through the anaerobic digestion of biodegradable organic material like segregated municipal waste, agricultural residue, press mud, spent wash, sewage sludge etc. Anaerobic digestion is a series of biological processes in which microorganisms break down biodegradable material in the absence of oxygen inside the digester. The digestion process begins with bacterial hydrolysis of the input materials like insoluble organic polymers such as carbohydrates, proteins, lipids, etc., and make them available for other bacteria. Acidogenic bacteria then convert these sugars and amino acids into carbon dioxide, hydrogen, ammonia, and organic acids. Acetogenic bacteria then convert these resulting organic acids into acetic acid, along with additional ammonia, hydrogen, and carbon dioxide. Finally, methanogens convert the intermediates into methane and carbon dioxide. The methane rich biogas can be used to produce electricity and heat or can be processed into renewable natural gas and transportation fuel.

The performance of anaerobic digestor significantly varies due to various factors such as irregular (low/high) solid loading, changes in feed composition, induction of any new contaminants or toxic substance in the system, sudden change in temperature, pH, salinity etc., and any other disturbance in the bioprocess.

Such disturbances adversely affect the performance of anaerobic digestion because it causes damage of microbial cells, disturbance in microbial metabolic pathways and decreased biotransformation of organic material leading to destabilize the digester and low biogas yield. Once disturbed the system takes 2-4 weeks to come to normal condition after such plant disturbance due to shock and sometime requires re-inoculation of microbe to achieve normal functioning of plant. This situation and delay may lead to inconsistent biogas production and process instability. Hence, there is need for means to maintain normal functioning of the plant and to reduce the time taken by plant to resume normalcy after plant disturbance due to above reasons.

The present invention discloses a novel composition useful for improving the stabilization of biodigester in terms of plant performance and gas yield. EP2683662 discloses production of a supplement complex particular for biomass that can be used for biogas production.

US 20120021476 relates to a trace element solution for the supplementing of nutrients for an anaerobic fermentation, in particular a biogas process, comprising at least one trace element and at least two complexing agents. Complexing agents are used which (1) are able to transport the trace elements in complexed form across the cell membrane and which (2) release the trace elements in the cell. Where applicable, the complexing agents are biologically decomposable.

U.S. Pat. No. 5,342,524 relates to addition of certain complexing agents to a substrate for anaerobic biogas fermentation, the solubility of the trace elements in the fermentation broth is increased, and that by this means the methane yield may be significantly improved.

US20120021476A1 relates to the addition of a trace element solution to an anaerobic reactor is disclosed. The trace elements are fed to the reactor as sulphate, chloride, selenate or molybdenum salts in aqueous solution, without regard to the bioavailability of the trace elements. In the presence of H2S the majority (>99.9%, see above) of the ions able to precipitate do so as sulphides. The nature of the anions of the trace element salt is not important for the bioavailability of the trace element concerned.

Commercially available trace element compositions, which are used as supplements for substrates, in particular for vegetable agricultural raw materials or industrial effluents, are used in quantities of approx. 1-2 kg/ton of dry substance of the substrates. Because of the heavy sulphide precipitation of the metals during fermentation, the fermentation residue may not be used as fertilizer, since the permitted metal concentration for fertilizer is far exceeded.

EP2592055 teaches the use of a trace element solution comprising at least a trace element and at least two chelating agents for metal ions, for supplementing nutrients for an anaerobic biogas fermentation, is claimed. Independent claims are included for: (1) the trace element solution; and (2) a process for the extraction of biogas in a biogas plant, comprising adding the trace element solution to the biogas plant, where the trace element solution contains at least one trace element and at least one chelating agent.

It can be seen that prior arts do not offer a solution which can ameliorate the effect of disturbances in plant operation due to factors such as irregular (low/high) solid loading, changes in feed composition, induction of any new contaminants or toxic substance in the system, sudden change in temperature, pH, salinity etc, any other disturbance in the bioprocess.

Present invention overcomes the deficiencies in the prior arts and provides a composition which ameliorates the effect of disturbances in plant operation due to various factors. The present invention can also be used simultaneously for fast recovery of microbial populations to maintain stabilized operation of the biomethanation plant producing consistent amount of gas without adversely affecting the quality of the liquid and solid manure.

SUMMARY OF THE INVENTION

This summary is provided to introduce a selection of concepts in a simple manner that is further described in the detailed description of the disclosure. This summary is not intended to identify key or essential inventive concepts of the subject matter nor is it intended for determining the scope of the disclosure.

The present invention provides a booster composition for enhancing the biogas yield and stabilizing the operation of a biomethanation plant, said composition comprising of: a) controlled release agents; b) redox potential balancers; c) direct interspecies electron transfer (DIET) improvers; d) micronutrient balancers; and e) Co-factors.

In one of the aspects, the present invention provides a booster composition for enhancing the biogas yield and stabilizing the operation of a biomethanation plant, said composition comprising of: a) controlled release agents; b) redox potential balancers; c) direct interspecies electron transfer (DIET) improvers; d) micronutrient balancers; and e) Co-factors, and wherein the controlled release agents are selected from the group consisting of aluminium silicate, chitosan, simethicone, CTAB or combinations thereof.

In one of the aspects, the present invention provides a booster composition for enhancing the biogas yield and stabilizing the operation of a biomethanation plant, said composition comprising of: a) controlled release agents; b) redox potential balancers; c) direct interspecies electron transfer (DIET) improvers; d) micronutrient balancers; and e) Co-factors, and wherein the redox potential balancers are selected from the group consisting of charcoal, $K_2HPO_4$, $KH_2PO_4$ or combinations thereof.

In one of the aspects, the present invention provides a booster composition for enhancing the biogas yield and stabilizing the operation of a biomethanation plant, said composition comprising of: a) controlled release agents; b) redox potential balancers; c) direct interspecies electron transfer (DIET) improvers; d) micronutrient balancers; and e) Co-factors, and wherein the DIET improvers are selected from the group consisting of iron oxide nano particle stabilized in Tetra methyl ammonium hydroxide, Al-Nano, Zn-Nano or combinations thereof.

In one of the aspects, the present invention provides a booster composition for enhancing the biogas yield and stabilizing the operation of a biomethanation plant, said composition comprising of: a) controlled release agents; b) redox potential balancers; c) direct interspecies electron transfer (DIET) improvers; d) micronutrient balancers; and e) Co-factors, and wherein the micronutrient balancers are selected from the group consisting of $NiCl_2$, $MnCl_2$, $MgNO_3$, $SeCl_2$, $CaCO_3$, $CuCl_2$ or combinations thereof.

In one of the aspects, the present invention provides a booster composition for enhancing the biogas yield and stabilizing the operation of a biomethanation plant, said composition comprising of: a) controlled release agents; b) redox potential balancers; c) direct interspecies electron transfer (DIET) improvers; d) micronutrient balancers; and e) Co-factors, and wherein the co-factors are selected from the group consisting of biotin, cyanocobalamine, pantothenic acid, thiamine, niacin or combinations thereof.

In one of the aspects, the present invention provides a booster composition for enhancing the biogas yield and stabilizing the operation of a biomethanation plant, said composition comprising of: a) 10810-13512 ppm of controlled release agents; b) 75500-88000 ppm of redox potential balancers; c) 5750-8200 ppm of direct interspecies electron transfer (DIET) improvers; d) 6825-8232 ppm of micronutrient balancers; and e) 167-260 ppm of Co-factors.

In one of the preferred aspects, the present invention provides a booster composition for enhancing the biogas yield and stabilizing the operation of a biomethanation plant, said composition comprising of: controlled release agents consist of aluminium silicate (10000 ppm), chitosan (1000 ppm), simethicone (10 ppm), CTAB (2000 ppm); a redox potential balancers consist of charcoal (2000 ppm), $K_2HPO_4$ (54000 ppm), $KH_2PO_4$ (26000 ppm); a DIET improvers consist of iron oxide nano particle stabilized in Tetra methyl ammonium hydroxide (5000 ppm), Al-Nano (1000 ppm), Zn-Nano (1000 ppm); a micronutrient balancers consist of $NiCl_2$ (2500 ppm), $MnCl_2$ (2000 ppm), $MgNO_3$ (2000 ppm), $SeCl_2$ (20 ppm), $CaCO_3$ (1000 ppm), $CuCl_2$ (10 ppm); and a Co-factor consist of biotin (50 ppm), cyanocobalamine (50 ppm), pantothenic acid (40 ppm), thiamine (30 ppm), niacin (10 ppm), and wherein the composition is made in 10% formic acid as base medium.

In another aspect, the present invention provides a method for enhancing the biogas yield and stabilizing the operation of a biomethanation plant, wherein said method is characterized in dosing the biomethanation plant with a booster composition comprising of: a) controlled release agents; b) redox potential balancers; c) direct interspecies electron transfer (DIET) improvers; d) micronutrient balancers; and e) Co-factors.

In one of the preferred aspects, the present invention provides a method for enhancing the biogas yield and stabilizing the operation of a biomethanation plant, wherein said method is characterized in dosing the biomethanation plant with a booster composition comprising of: a) controlled release agents; b) redox potential balancers; c) direct interspecies electron transfer (DIET) improvers; d) micronutrient balancers; and e) Co-factors and wherein the dose of booster composition is 25-100 ml/ton of feedstock in the biomethanation plant.

In one of the preferred aspects, the present invention provides a method for enhancing the biogas yield and stabilizing the operation of a biomethanation plant, wherein the biomethanation plant is provided with first dose of booster composition at completion of one week of operation after addition of biomethanation inoculum and subsequent doses are provided at a gap interval of 2-3 weeks.

In another aspect, the present invention provides a method for the preparation of booster composition for enhancing the biogas yield and stabilizing the operation of a biomethanation plant, wherein said method comprises steps of: a) preparing separate solutions of controlled release agents; redox potential balancers, direct interspecies electron transfer (DIET) improvers, micronutrient balancers, and co-factors, in 10% formic acid as base medium; b) mixing solution of direct interspecies electron transfer (DIET) improvers obtained in step a) with the solution of controlled release agents obtained in step a) at an addition rate of 2.5 ml/min with continuous stirring; c) mixing solution of co-factors obtained in step a) to the mixture solution obtained in step b) at an addition rate of 0.6 ml/min with continuous stirring; d) mixing solution of solution of redox potential balancers obtained in step a) to the mixture solution obtained in step c) at an addition rate of 5 ml/min with stirring; e) mixing solution of solution of micronutrient balancers obtained in step a) to the mixture solution obtained in step d) at an addition rate of 0.2 ml/min with stirring; and f) making up the final volume of booster composition solution obtained in step e) to 1 L using 10% formic acid.

DESCRIPTION OF THE ACCOMPANYING DRAWINGS

FIGS. 7A and 7B: shows the recovery pattern of biogas yield from different feed of biomass waste receiving temperature or pH shock in presence of booster: A: Recovery pattern of biogas yield with kitchen waste as feedstock and receiving pH shock, B: Recovery pattern of biogas yield with kitchen waste as feedstock and receiving temperature shock, C: Recovery pattern of biogas yield with biomass (Paddy straw) waste as feedstock and receiving pH shock, D: Recovery pattern of biogas yield with biomass (Paddy straw) waste as feedstock and receiving temperature shock, E: Recovery pattern of biogas yield with press mud as feedstock and receiving pH shock, F: Recovery pattern of biogas yield with press mud as feedstock and receiving temperature shock, G: Recovery pattern of biogas yield with cattle dung as feedstock and receiving pH shock, H: Recovery pattern of biogas yield with cattle dung as feedstock and receiving temperature shock, I: Recovery pattern of biogas yield with MSW as feedstock and receiving pH shock, J: Recovery pattern of biogas yield with MSW as feedstock and receiving temperature shock.

DETAILED DESCRIPTION OF THE INVENTION

While the invention is susceptible to variations and modifications other than those specifically described herein by specific embodiments and examples. It is to be understood that the present disclosure includes all modifications, equivalents, and alternative falling within the spirit and the scope of the invention as defined by the appended claims.

The figures and protocols have been represented where appropriate by conventional representations, showing only those specific details that are pertinent to understanding of the embodiments of the present invention and not to obscure the disclosure with details that will be readily apparent to those of ordinary skill in the art having benefit of the description herein.

Unless defined otherwise, all technical and scientific terms used herein have the same meaning as commonly understood by one of ordinary skill in the art to which this disclosure belongs. Although any methods and materials similar or equivalent to those described herein can be used in the practice for testing of the disclosure.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particulars and all details set forth herein are used in the context of some embodiments and therefore should not be necessarily taken as limiting factors to the attached claims. The attached claims and their legal equivalents can be realized in the context of embodiments other than the ones used as illustrative examples in the description below.

The present invention discloses a booster composition for improving the biogas yield in a biomethanation plant and for aiding in fast recovery of microbial populations to maintain stabilized operation of the biomethanation plant.

In accordance with the present invention, a composition is provided for improve the biogas yield and stabilize biomethanation plant operation comprising controlled release agents, redox potential balancers, direct interspecies electron transfer (DIET) improvers, micronutrient balancers, and Co-factors for desired enzyme activity.

In accordance with the present invention, the controlled release agents include, but are not limited to Aluminium Silicate, Chitosan, Simethicone, CTAB or combinations thereof. In accordance with the present invention, the redox potential balancers include, but are not limited to Charcoal, $K_2HPO_4$, $KH_2PO_4$ or combinations thereof.

The direct interspecies electron transfer (DIET) improvers include, but are not limited to, Iron oxide nano particle stabilized in Tetra methyl ammonium hydroxide, Al-Nano, Zn-Nano or combinations thereof.

Non-limiting examples of the micronutrient balancers used in accordance with the present invention include $NiCl_2$, $MnCl_2$, $MgNO_3$, $SeCl_2$, $CaCO_3$, $CuCl_2$ or combinations thereof.

Co-factors for desired enzyme activity used in accordance with the present invention include, but are not limited to biotin, cyanocobalamine, pantothenic acid, thiamine, niacin or combinations thereof.

The composition as disclosed in the present invention is dosed in the inlet of biodigester 25-100 ml/ton feedstock at a frequency of 2-3-times in a week. It is feed agnostic and helps in hydrolysis, acidogenesis, acetogenesis, and methanogenesis. The composition can be useful in one stage, two stage, or multistage biomethanation process.

Present invention can be used for covered anaerobic lagoon digester, plug flow digester, complete mix digester, dry digester or CSTR based digester. In an embodiment, the composition can be used in any digester maintaining 05-80 degree C.

Composition disclosed in the present invention is useful even if the only 1-10 CFU/ml living cells are available in the system. It improves the characteristics of the liquid and solid manure from the reactor. In an embodiment the composition needs continuous dosing. In another embodiment, the composition can be used intermittently also. The composition works well with all type of biogas inoculum.

In accordance with the present invention, a method for preparation of booster composition is provided comprising the steps of:

1) Dissolving separately each of components of the group comprising the controlled release agents, redox potential balancers, direct interspecies electron transfer (DIET) improvers, micronutrient balancers, and Co-factors for desired enzyme activity in 100 ml of 10% formic acid as base medium;
2) Solution of direct interspecies electron transfer (DIET) improvers obtained in step 1 is mixed with solution of controlled release agents obtained in step 1 at an addition rate of 2.5 ml/min with continuous stirring at 250 rpm;
3) To the mixture solution obtained in step 2, solution of Co-factors obtained in step 1 are added at a rate of 0.6 ml/min, followed by addition of solution of redox potential balancers obtained in step 1 at a rate of 5 ml/min with stirring; and
4) Solution of micronutrient balancers obtained in step 1 were added to mixture solution obtained at step 3 at a rate of 0.2 ml/min and the final volume was made to 1 L using 10% formic acid.

Having described the basic aspects of the present invention, the following non-limiting examples illustrate specific embodiment thereof.

Example 1: Development of Booster Composition for Improving Biogas Yield and Stabilizing Biomethanation Plant Operation I. Substrates and Inoculum All the experiments were conducted using organic/food waste. The non-biodegradable components were manually removed from the food waste and then the waste was homogenized using a blender. The homogenized food waste was added into the reactors according to the required organic loading rate (OLR). The biomethanation inoculum used for the biomethanation experiment consists of microbial blend of active microbial culture as described in detail in Indian patent application No 201921037470 dated Sep. 17, 2019, which herein is incorporated by reference. Said active microbial culture was grown anaerobically at 37° C. for 7 days and added to the reactors. The microbes include individually or in combinations but not limited to *Brevibacterium* sp. MTCC 25255; *Clostridium* sp. MTCC 25264; *Methanobacterium* sp. MTCC 25266; *Methanothermobacter* sp. MTCC 25268; *Methanosarcina* sp. MTCC 25300; *Desulfovibrio* sp. MTCC 25301; *Methanolobus* sp. MTCC 25302; *Methanosaeta* sp. MTCC 25303; *Thermotoga* sp. MTCC 25304; *Pyrococcus* sp. MTCC 25305; *Shewanella* sp. MTCC 25020, *Moorella* sp. MTCC 25267, *Lactobacillus* sp. MTCC 25282.

II. Preparation of Booster Composition

The booster composition composed five different groups of chemical components:
- Group-A: controlled release agents,
- Group-B: redox potential balancers,
- Group-C: direct interspecies electron transfer (DIET) improvers,
- Group-D: micronutrient balancers,
- Group-E: Co-factor for desired enzyme activity.

To prepare booster composition components from Group A-E were mixed in appropriate concentration as per table-1 and as per the method disclosed in the description. The prepared booster was stored at 4° C. prior to use.

TABLE 1

Components of booster composition

| Component | Concentration in (ppm) |
|---|---|
| (Group-A) Components for controlled release | |
| Aluminium Silicate | 8000-10000 |
| Chitosan | 800-1000 |
| Simethicone | 10-12 |
| CTAB | 2000-2500 |
| (Group-B) Components for balancing the redox potential | |
| Bio-Charcoal | 1500-2000 |
| $K_2HPO_4$ | 54000-60000 |
| $KH_2PO_4$ | 20000-26000 |
| (Group-C) Components for improving the direct interspecies electron transfer (DIET) | |
| Iron oxide nano particle stabilized in Tetra methyl ammonium hydroxide | 4000-6000 |
| Al-Nano | 750-1000 |
| Zn-Nano | 1000-1200 |
| (Group-D) Components for micronutrient balance | |
| $NiCl_2$ | 2000-2500 |
| $MnCl_2$ | 2000-2200 |
| $MgNO_3$ | 2000-2500 |
| $SeCl_2$ | 15-20 |
| $CaCO_3$ | 800-1000 |
| $CuCl_2$ | 10-12 |
| (Group-E) Co-factor for desired enzyme activity | |
| Biotin | 40-60 |
| Cyanocobalamine | 50-70 |
| Pantothenic acid | 40-60 |
| Thiamine | 30-60 |
| Niacin | 7-10 |

In preferred embodiment the booster composition comprises components of Group A-E in the concentration given in Table 1-A.

TABLE 1-A

Preferred booster composition

| Component | Concentration in (ppm) |
|---|---|
| (Group-A) Components for controlled release | |
| Aluminium Silicate | 10000 |
| Chitosan | 1000 |
| Simethicone | 10 |
| CTAB | 2000 |
| (Group-B) Components for balancing the redox potential | |
| Bio-Charcoal | 2000 |
| $K_2HPO_4$ | 54000 |
| $KH_2PO_4$ | 26000 |
| (Group-C) Components for improving the direct interspecies electron transfer (DIET) | |
| Iron oxide nano particle stabilized in Tetra methyl ammonium hydroxide | 5000 |
| Al-Nano | 1000 |
| Zn-Nano | 1000 |
| (Group-D) Components for micronutrient balance | |
| $NiCl_2$ | 2500 |
| $MnCl_2$ | 2000 |
| $MgNO_3$ | 2000 |
| $SeCl_2$ | 20 |
| $CaCO_3$ | 1000 |
| $CuCl_2$ | 10 |
| (Group-E) Co-factor for desired enzyme activity | |
| Biotin | 50 |
| Cyanocobalamine | 50 |
| Pantothenic acid | 40 |
| Thiamine | 30 |
| Niacin | 10 |

III. Experimental Setup for Booster Composition Promoted Biomethanation.

Experiment was carried out in a series of sealed glass digesters (Total/Working volume, 1/0.8 L) at 37° C. Kitchen/organic waste was used as feedstock after shredding/grinding. Organic loading was fixed at 15% TS content for all the experiments and was fed to bioreactor/digesters along with designated amount of water. 10% (v/v) biomethanation inoculum was added to the bioreactor and operated under strict anaerobic condition. All the reactors were closed airtight and flushed with $N_2$ after feed addition to create anaerobic environment and to avoid gaseous exchange. After 1 week of operation, the bioreactors were dosed with different booster composition (conc. 25 ml/ton) components as given in Table 2. The total biogas yield was calculated at various time intervals and presented as m3/ton of waste.

TABLE 2

Biogas Yield using booster composition.

| Biogas Yield (%) | Biogas Yield (m3/ton of waste) | | |
|---|---|---|---|
| | $21^{st}$ day | $30^{th}$ Day | $45^{th}$ day |
| Control (no booster) | 91 ± 2 | 96 ± 2 | 98 ± 2 |
| Gr-A | 94 ± 2 | 95 ± 2 | 99 ± 2 |
| Gr-B | 98 ± 2 | 94 ± 2 | 95 ± 2 |
| Gr-C | 95 ± 2 | 93 ± 2 | 97 ± 2 |
| Gr-D | 92 ± 2 | 94 ± 2 | 98 ± 2 |
| Gr-E | 102 ± 2 | 108 ± 2 | 107 ± 2 |
| Gr-A + Gr-B | 107 ± 2 | 110 ± 2 | 115 ± 2 |
| Gr-A + Gr-C | 108 ± 2 | 112 ± 2 | 113 ± 2 |
| Gr-A + Gr-D | 109 ± 2 | 115 ± 2 | 114 ± 2 |

TABLE 2-continued

Biogas Yield using booster composition.

| Biogas Yield (%) | Biogas Yield (m3/ton of waste) | | |
|---|---|---|---|
| | 21$^{st}$ day | 30$^{th}$ Day | 45$^{th}$ day |
| Gr-A + Gr-E | 112 ± 2 | 114 ± 2 | 117 ± 2 |
| Gr-B + Gr-C | 103 ± 2 | 105 ± 2 | 108 ± 2 |
| Gr-B + Gr-D | 104 ± 2 | 104 ± 2 | 108 ± 2 |
| Gr-B + Gr-E | 105 ± 2 | 108 ± 2 | 109 ± 2 |
| Gr-C + Gr-D | 110 ± 2 | 109 ± 2 | 98 ± 2 |
| Gr-C + Gr-E | 113 ± 2 | 99 ± 2 | 100 ± 2 |
| Gr-A + Gr-B + Gr-C | 110 ± 2 | 108 ± 2 | 107 ± 2 |
| Gr-A + Gr-B + Gr-D | 98 ± 2 | 112 ± 2 | 112 ± 2 |
| Gr-A + Gr-B + Gr-E | 102 ± 2 | 108 ± 2 | 107 ± 2 |
| Gr-B + Gr-C + Gr-D | 99 ± 2 | 100 ± 2 | 106 ± 2 |
| Gr-B + Gr-C + Gr-E | 102 ± 2 | 107 ± 2 | 100 ± 2 |
| Gr-A + Gr-B + Gr-C + Gr-D | 114 ± 2 | 112 ± 2 | 117 ± 2 |
| Gr-A + Gr-B + Gr-C + Gr-E | 118 ± 2 | 117 ± 2 | 115 ± 2 |
| Gr-A + Gr-B + Gr-C + Gr-D + Gr-E (Booster) | 153 ± 2 | 157 ± 2 | 154 ± 2 |

Example 2: Study of Controlled Release of Micronutrients from Booster Composition Controlled release of the micronutrients over time is very important to maintain sustained microbial population during anaerobic digestion. The micronutrients described in group-D are adsorbed in Group-A support materials. The adsorbed micronutrients (trace elements) are slow released to provide optimal bioavailability to the microorganisms for longer duration. The effect of the released percentage of micronutrient ions over time in pure water environment had been studied systematically (Table 3). Initially, 25 ml of booster composition was added to 800 ml of deionized water (DI) and the leaching of metal to the aqueous medium was analyzed via ICP-AES analysis. The microbial population was also counted as cfu/ml from both the operating bioreactor that is dosed with booster composition (25 ml/ton) and control (without booster composition).

The results confirmed the slow-release phenomenon of micronutrients from booster composition and demonstrated that components described in group-A could regulate the dissolution rate of nutrient ions via slow-release mechanism. As a result, Group-D components have enhanced availability for the microbial communities in the biomethanation process.

TABLE 3

Release of metal components of micronutrients over time

| Days | 3$^{rd}$ | 5$^{th}$ | 8$^{th}$ | 10$^{th}$ | 21$^{st}$ |
|---|---|---|---|---|---|
| % Release of total metals (Ni + Mn + Mg + Se + Cu) from Booster | 10 | 19 | 33 | 55 | 98 |
| Microbial Population (CFU) with Booster | 5.2 × 10$^{11}$ | 7.8 × 10$^{11}$ | 6.7 × 10$^{11}$ | 5.9 × 10$^{11}$ | 9.8 × 10$^{11}$ |
| Microbial Population (CFU) without Booster | 3.8 × 10$^{10}$ | 8.9 × 10$^{8}$ | 5.6 × 10$^{7}$ | 8.3 × 10$^{7}$ | 3.4 × 10$^{6}$ |

Example 3: Evaluation of Booster Composition Performance During Shock and Destabilized Conditions The performance of Booster composition was evaluated using organic waste under continuous mode as well as pH and thermal shock conditions. The organic waste obtained was segregated for any non-biodegradable material and grinded before use. Experiment was carried out in a series of sealed glass digesters (Total/Working volume, 1/0.8 L) at a Total solid (TS) loading rate of 15% and after adjusting the initial pH 7.0. Experiment was carried out under anaerobic condition at 37 degree C. for 8 days. Then, the reactor was added with 10% (v/v) of biomethanation inoculum for carrying out biomethanation. Performance of the reactor was monitored based on biogas yield and COD change. Experiment was carried out in two parts, i.e., continuous operation for long term (more than 100 days) and recovery after shock load to see the impact of booster composition addition. Shock load was studied with respect to pH (sudden drop in pH up to 5.0) and temperature (sudden drop in temperature up to 5 degree C. for 2 h). In continuous mode of operation, booster composition was dosed at 0.025 ml/L at intervals of twice a week, while in shock load conditions, the dose is increased to 0.25 ml/L for the first 3 doses per week up to 3-4 weeks after shock, followed by normal schedule.

Figure 1:
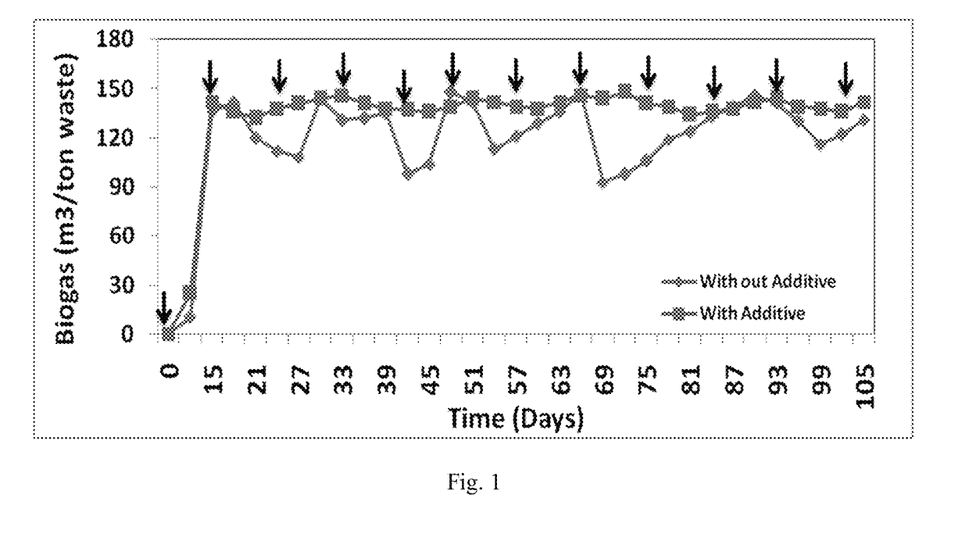
FIG. 1: shows the biogas yields during continuous operation of the digester showing significant positive impact of adding the booster composition.
Figure 2:
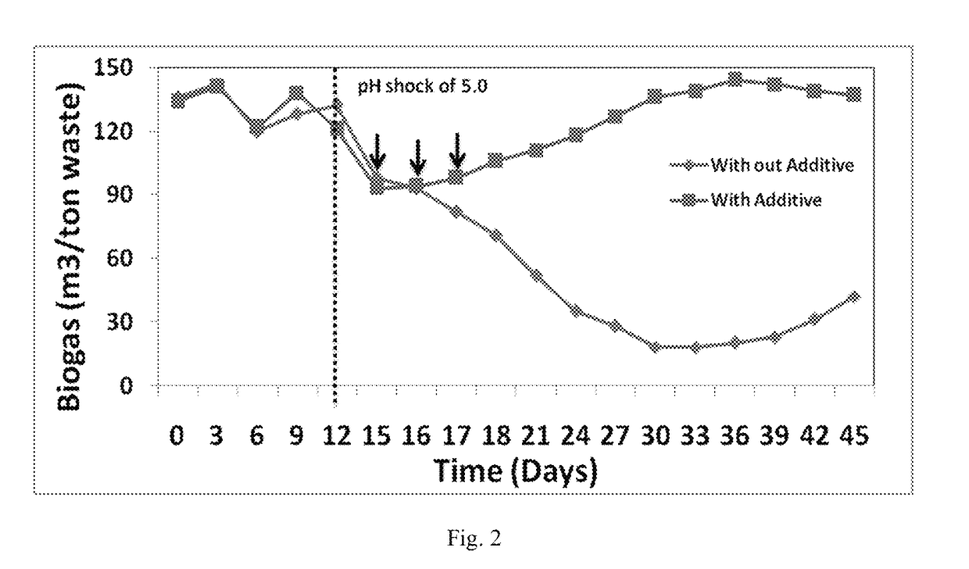
FIG. 2: shows the recovery pattern of biogas yield after pH shock in presence of booster composition.

A clear demarcation in the results obtained among the experiments carried out with and without booster composition can be seen in FIG. 1. Further, the experiment on sudden pH shock has also showed faster recovery of biogas yield in presence of booster composition, while the experiment without booster composition has took 2-4 weeks to start showing increment in the biogas yield (FIG. 2).

Figure 3:
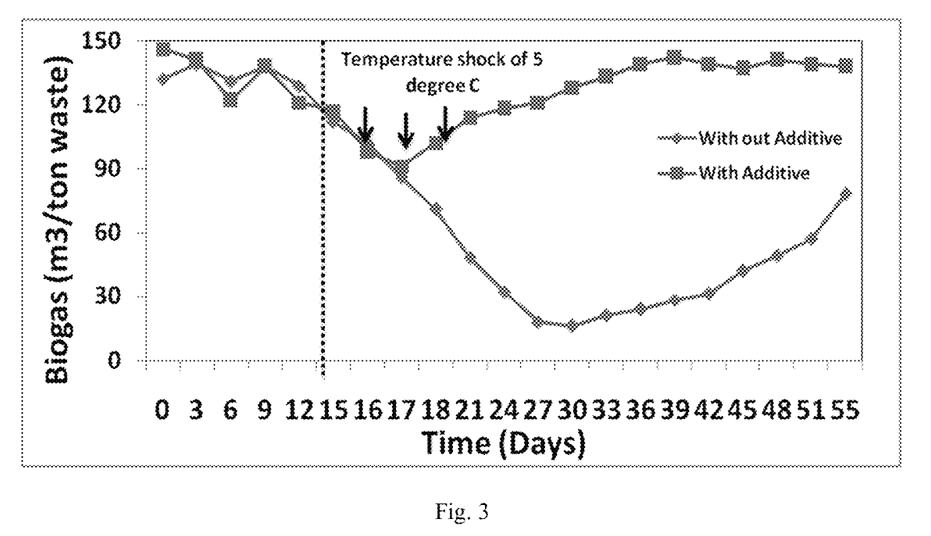
FIG. 3: shows the recovery pattern of biogas yield with after temperature shock in presence of booster composition.

Subsequently, experiment on impact of booster composition against sudden temperature shock was carried out which has also showed faster recovery of biogas yield in presence of -booster composition, while the experiment without booster composition has took more than 4 weeks to start showing increment in the biogas yield (FIG. 3).

Figure 4:
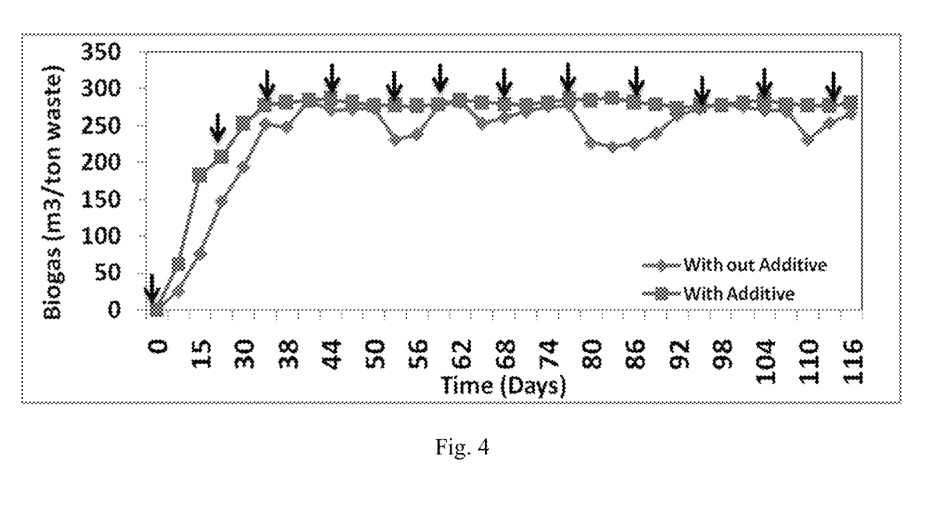
FIG. 4: shows the continuous mode operation of biodigester with biomass waste.

To study the performance of booster composition with respect to feedstock nature, complex feedstock, i.e., paddy straw biomass was used to study all the aspects that were evaluated with kitchen waste. The dosing pattern of booster composition was also kept at similar conditions. Continuous operation in presence of booster composition for more than 100 days has shown significant stability in biogas yield, while the biogas yield was inconsistent and lower in the absence of booster composition (FIG. 4).

Figure 5:
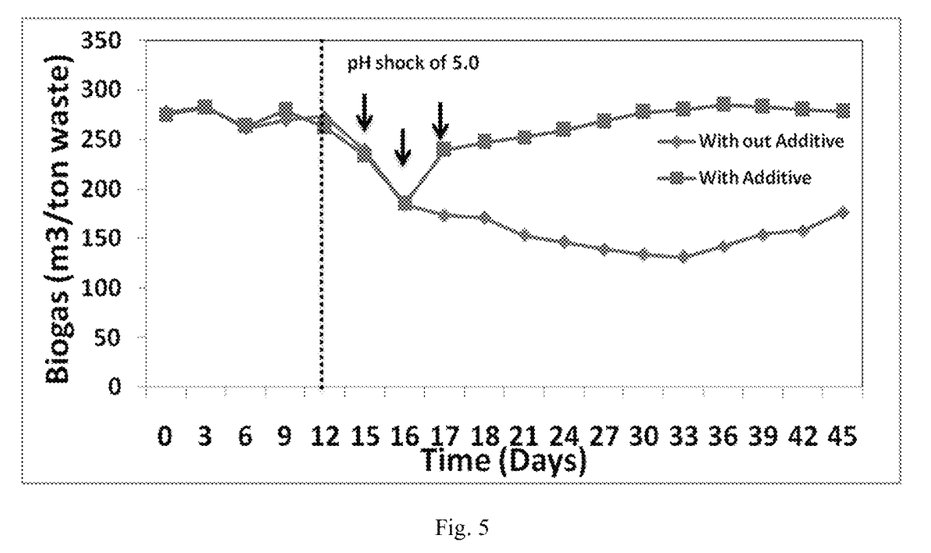
FIG. 5: shows the recovery pattern of biogas yield from biomass waste after pH shock in presence of Booster.
Figure 6:
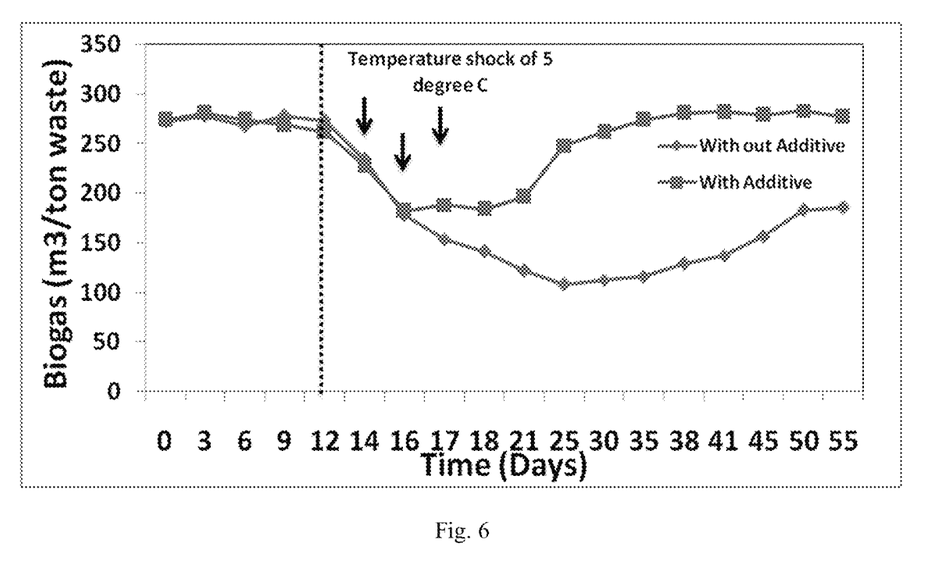
FIG. 6: shows the recovery pattern of biogas yield from biomass waste after temperature shock in presence of Booster.

Further studies on pH and temperature shock also showed faster recovery of the biogas yield in presence of booster composition (FIGS. 5 and 6), indicating a positive impact of booster composition on biomethanation.

In addition to the consistent and increased biogas yield, booster composition also enhanced the COD reduction, indicating the higher waste conversion efficiency. Table 4 depicted the COD removal efficiencies with respect to both organic and biomass waste in presence and absence of booster composition during the continuous mode operation.

TABLE 4

COD removal efficiencies with respect to organic and biomass waste

% COD REDUCTION

| | Kitchen waste | | Biomass waste | |
|---|---|---|---|---|
| Day | Without Booster | With Booster | Without Booster | With Booster |
| 15 | 52.8% | 69.1% | 47.8% | 59.2% |
| 25 | 54.6% | 71.3% | 49.1% | 65.3% |
| 30 | 58.1% | 73.6% | 51.6% | 69.1% |
| 35 | 57.8% | 74.1% | 53.7% | 70.5% |
| 40 | 58.3% | 73.8% | 54.6% | 71.7% |
| 45 | 58.1% | 73.3% | 53.9% | 71.4% |

Further to that, the characteristics of the solid and liquid manure obtained after biomethanation has also been improved when the booster composition was used due to the release of essential trace metals and other constituents that are required for soil fertility. Table 5 and 6 depicted the improvement in the characteristics of the solid/liquid manure, especially pertaining to the N, P, K and trace element components that are essentially required for soil fertility.

TABLE 5

Characteristics of manure obtained after biomethanation of kitchen waste.

| Test/Parameter | Without Booster | With Booster |
|---|---|---|
| pH | 7.1 | 6.9 |
| Electrical conductivity (dS/m) | 2.6 | 3.1 |
| Moisture (% w/w) | 21.4 | 21.8 |
| Bulk density (g/cm3) | 0.78 | 0.81 |
| Total Organic Carbon (g/kg) | 21 | 24 |
| Total Nitrogen (% w/w) | 1.8 | 2.3 |
| Total Phosphorous (% w/w) | 0.57 | 0.71 |
| Potassium content (% w/w) | 0.69 | 0.87 |
| Total N, P, K (% w/w) | 3.08 | 3.88 |
| C/N ratio | 11.67 | 10.44 |
| Pathogen | Nil | Nil |
| Arsenic (ppm) | ND* | ND* |
| Cadmium (ppm) | ND* | ND* |
| Chromium (ppm) | 6.0 | 7.3 |
| Copper (ppm) | 164 | 216 |
| Nickel (ppm) | 18 | 37 |
| Zinc (ppm) | 216 | 742 |
| Mercury (ppm) | ND* | ND* |

*ND—Not Detected

TABLE 6

Characteristics of manure obtained after biomethanation of biomass waste.

| Test/Parameter | Without Booster | With Booster |
|---|---|---|
| pH | 6.9 | 6.8 |
| Electrical conductivity (dS/m) | 1.8 | 2.9 |
| Moisture (% w/w) | 22.6 | 23.1 |
| Bulk density (g/cm3) | 0.63 | 0.72 |
| Total Organic Carbon (g/kg) | 23.1 | 24.2 |
| Total Nitrogen (% w/w) | 1.8 | 2.1 |
| Total Phosphorous (% w/w) | 0.51 | 0.69 |
| Potassium content (% w/w) | 0.71 | 0.88 |
| Total N, P, K (% w/w) | 3.02 | 3.67 |
| C/N ratio | 12.83 | 11.52 |
| Pathogen | Nil | Nil |
| Arsenic (ppm) | 2.2 | 2.1 |
| Cadmium (ppm) | ND | ND |
| Chromium (ppm) | 7.2 | 7.1 |
| Copper (ppm) | 251 | 284 |
| Nickel (ppm) | 8 | 32 |
| Zinc (ppm) | 127 | 698 |
| Mercury (ppm) | ND | ND |

*ND—Not Detected

Overall, the addition of Booster has significant positive impact on the biogas yield, consistency in biogas production, protection from shock loads/operating conditions, COD reduction and the manure quality.

Example 4: Evaluation of Booster Performance at Different Concentrations of its Components and Different Feedstock During Shock and Destabilized Conditions The performance of booster composition under different concentrations of its components was evaluated using different types of organic waste under continuous mode of operation as well as pH and thermal shock conditions. Different wastes used for experiments include, kitchen waste, paddy straw, press mud, cattle dung and municipal solid waste (MSW). All the wastes were segregated for any non-biodegradable material and were grinded before use, except cattle dung. Experiment was carried out in continuous mode in sealed glass digesters (Total/Working volume, 1/0.8 L) at a total solid (TS) loading rate of 15% and after adjusting the initial pH 7.0. Paddy straw (biomass) and press mud were added with cattle dung for balancing C/N ratio as well as pH at a rate of 20% and 40% respectively. All other organic wastes were used as such, and the final TS of the feed slurry was maintained at 15%. Experiments were carried out under anaerobic condition at 37 degree C. after addition of 10% (v/v) of biomethanation inoculums. All the reactors were closed airtight and maintained under anaerobic environment to avoid gaseous exchange. After 1 week of continuous operation, the bioreactors were dosed with different booster composition (conc. 25 ml/ton) components as given in Table 7. The total biogas yield was calculated at various time intervals and presented as m3/ton of waste.

TABLE 7

Different booster compositions for different experimental compositions

| Component | Exp 1(A) | Exp 2 (B) | Exp 3 (C) | Exp 4 (D) | Exp 5 (E) | Exp 6 (F) | Exp 7 (G) | Exp 8 (H) | Exp 9 (I) | Exp 10 (J) |
|---|---|---|---|---|---|---|---|---|---|---|
| Aluminium Silicate | 8000 | 9000 | 8500 | 10000 | 9200 | 8600 | 8200 | 9100 | 9700 | 8900 |
| Chitosan | 900 | 950 | 800 | 840 | 910 | 1000 | 990 | 810 | 970 | 850 |
| Simethicone | 10 | 10.5 | 12 | 11.4 | 11.9 | 12 | 10 | 11.5 | 10.5 | 10 |
| CTAB | 2000 | 2500 | 2200 | 2400 | 2000 | 2100 | 2500 | 2000 | 2400 | 2500 |
| Bio-Charcoal | 1800 | 1900 | 2000 | 1500 | 1600 | 1700 | 1500 | 2000 | 1900 | 1600 |
| K2HPO4 | 54000 | 59000 | 56500 | 54500 | 55000 | 58000 | 57600 | 59200 | 60000 | 59500 |
| KH2PO4 | 26000 | 21000 | 23500 | 25500 | 25000 | 22000 | 22400 | 21800 | 20000 | 20500 |
| Iron oxide nano particle stabilized in Tetra methyl ammonium hydroxide | 5500 | 4800 | 4200 | 5600 | 4000 | 4400 | 6000 | 5900 | 5100 | 4200 |
| Al-Nano | 750 | 800 | 850 | 900 | 950 | 1000 | 780 | 920 | 840 | 790 |
| Zn-Nano | 1100 | 1200 | 1150 | 1050 | 1080 | 1020 | 1000 | 1060 | 1130 | 1200 |
| NiCl2 | 2100 | 2400 | 2200 | 2500 | 2000 | 2300 | 2500 | 2000 | 2200 | 2300 |
| MnCl2 | 2000 | 2050 | 2150 | 2200 | 2100 | 2060 | 2140 | 2190 | 2070 | 2020 |
| MgNO3 | 2100 | 2400 | 2450 | 2200 | 2150 | 2000 | 2500 | 2300 | 2350 | 2200 |
| SeCl2 | 16 | 18 | 17 | 19 | 15 | 20 | 16 | 18 | 17 | 20 |
| CaCO3 | 950 | 850 | 800 | 900 | 1000 | 820 | 960 | 910 | 830 | 800 |
| CuCl2 | 10 | 10.5 | 12 | 10.9 | 11 | 11.5 | 11.8 | 10 | 11 | 12 |
| Biotin | 45 | 60 | 55 | 50 | 40 | 45 | 40 | 50 | 55 | 60 |
| Cyanocobalamine | 60 | 65 | 50 | 55 | 60 | 70 | 50 | 60 | 70 | 55 |
| Pantothenic acid | 45 | 55 | 60 | 50 | 40 | 45 | 50 | 60 | 55 | 60 |
| Thiamine | 30 | 35 | 40 | 45 | 50 | 55 | 60 | 55 | 35 | 45 |
| Niacin | 7 | 9 | 8 | 7 | 9 | 10 | 7 | 10 | 9 | 10 |
| Organic waste used for experiment | Kitchen waste | | Biomass (Paddy straw) waste | | Press mud | | Cattle dung | | MSW | |

Performance of all the experimental variations was monitored based on biogas yield. All experiments were carried out to evaluate the booster performance for recovery of biogas yield after shock-load. Shock load was studied with respect to pH (sudden drop in pH up to 5.0) and temperature (sudden drop in temperature up to 5 degree C. for 2 h). The designated booster composition was dosed at 0.25 ml/L for 3 doses per week up to 3-4 weeks after shock, followed by 0.025 ml/L, twice a week.

Figure 7A:
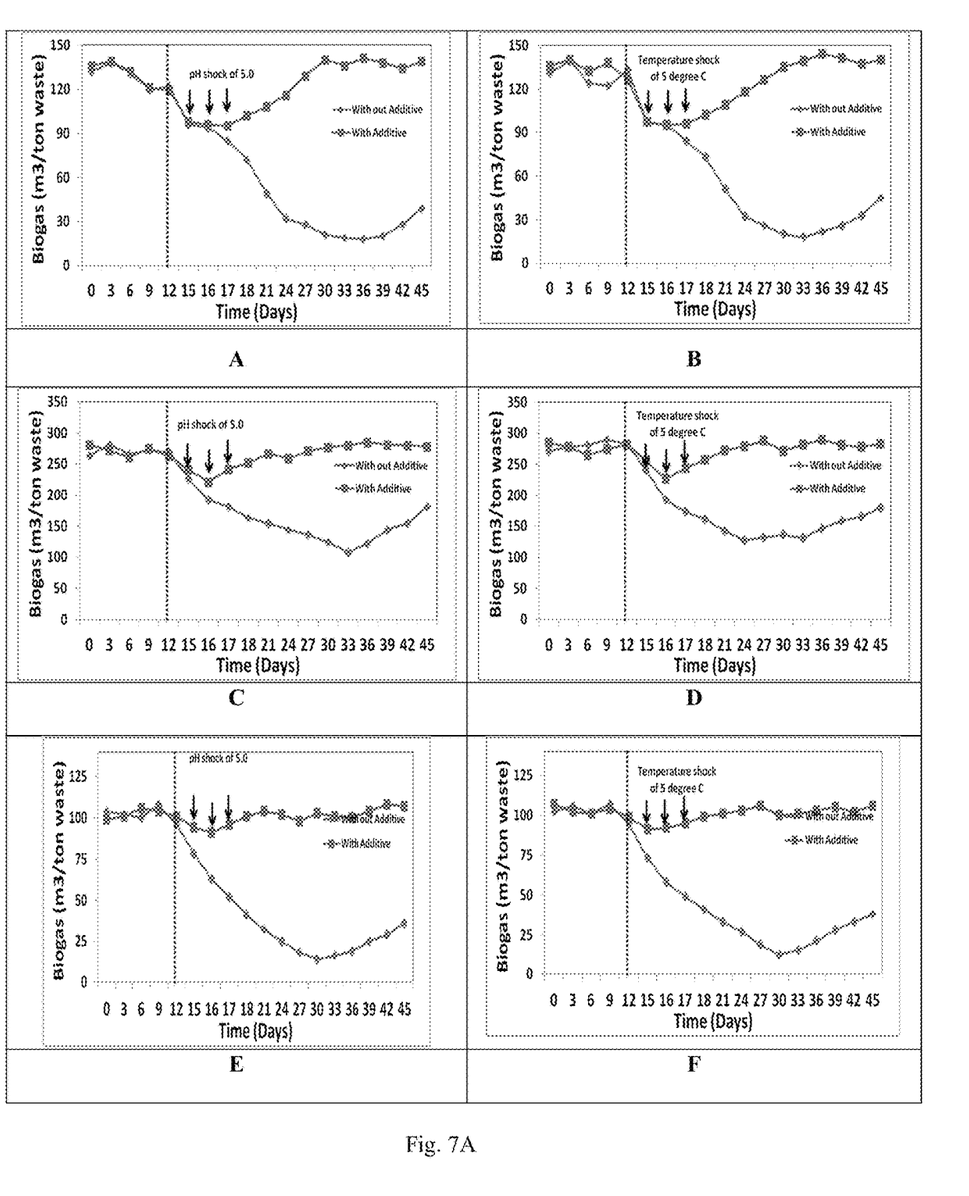
Figure 7B:
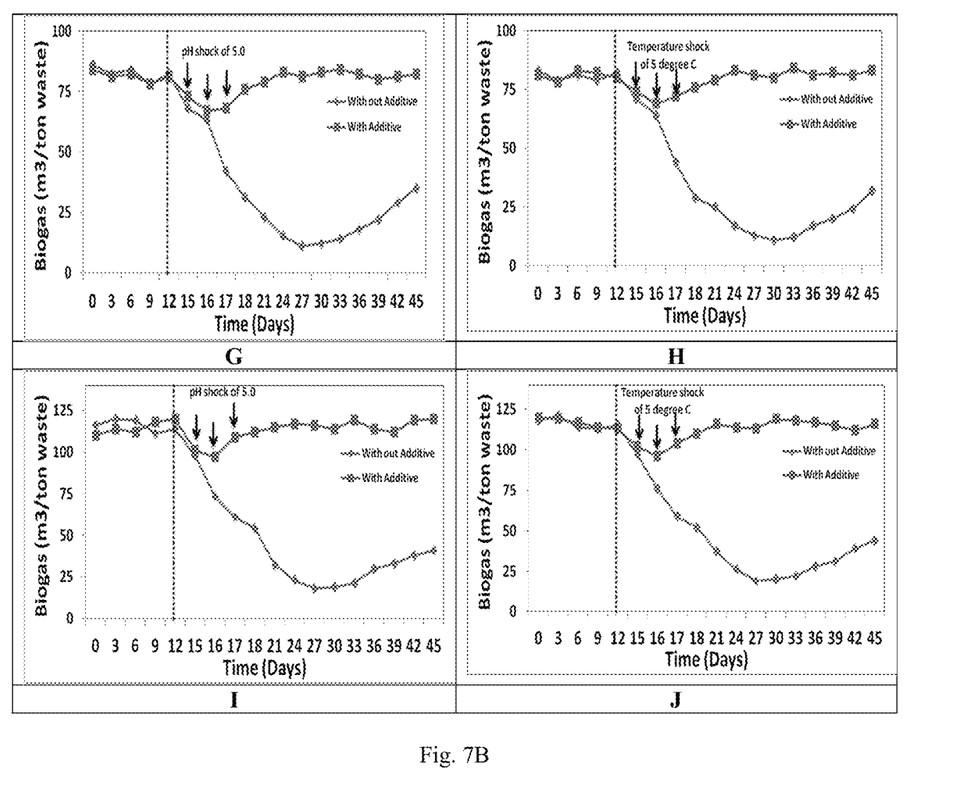

A clear demarcation in the results obtained among the experiments carried out with and without booster composition can be seen in FIG. 7. All the experimental combinations with different types of waste have shown significant stable performance of biogas yield after sudden pH and temperature shock. The experiments with booster dosing showed immediate recovery of biogas yield, while the experiment without booster composition has taken 2-4 weeks to start showing increment in the biogas yield.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the sequential actions need not be implemented strictly as shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, process parameters and use of material, are possible. The scope of embodiments is at least as broad as given by the following claims.

We claim:

1. A method for enhancing biogas yield and stabilizing an operation of a biomethanation plant, the method comprising:
   homogenizing organic waste;
   loading water and the organic waste into a digester of the biomethanation plant at an organic loading rate of about 15% total solid content;
   adding a biomethanation inoculum;
   airtightly closing the digester and flushing with an inert gas to create an anaerobic environment and to avoid a gaseous exchange;
   preparing a booster composition; and
   dosing the digester with the booster composition at completion of one week of the operation after addition of the biomethanation inoculum, wherein the booster composition comprises:
   controlled release agents, comprising 10000 ppm of aluminium silicate, 1000 ppm of chitosan, 10 ppm of simethicone, and 2000 ppm of CTAB;
   redox potential balancers, comprising 2000 ppm of charcoal, 54000 ppm of $K_2HPO_4$, and 26000 ppm of $KH_2PO_4$;
   direct interspecies electron transfer (DIET) improvers comprising 5000 ppm of iron oxide nano particles particle stabilized in Tetra methyl ammonium hydroxide, 1000 ppm of Al-Nano, and 1000 ppm of Zn- Nano;
   micronutrient balancers comprising 2500 ppm of $NiCl_2$, 2000 ppm of $MnCl_2$, 2000 ppm of $MgNO_3$, 20 ppm of $SeCl_2$, 1000 ppm of $CaCO_3$, and 10 ppm of $CuCl_2$; and
   co-factors comprising 50 ppm of biotin, 50 ppm of cyanocobalamine, 40 ppm of pantothenic acid, 30 ppm of thiamine, and 10 ppm of niacin, and wherein the composition is made in 10% formic acid as a base medium.

2. The method as claimed in claim 1, further comprising subsequently dosing the digester with the booster composition at a gap interval of 2-3 weeks.

3. A method for preparation of a booster composition for enhancing biogas yield and stabilizing an operation of a biomethanation plant, the method comprising:
    preparing a solution of controlled release agents, a solution of redox potential balancers, a solution of direct interspecies electron transfer (DIET) improvers, a solution of micronutrient balancers, and a solution of co-factors, wherein each solution is prepared in 10% formic acid as a base medium;
    mixing the solution of the DIET improvers with the solution of the controlled release agents at an addition rate of 2.5 ml/min with continuous stirring to form a first mixture;
    mixing the solution of the co-factors with the first mixture at an addition rate of 0.6 ml/min with continuous stirring to form a second mixture;
    mixing the solution of the redox potential balancers with the second mixture at an addition rate of 5 ml/min with stirring to form a third mixture;
    mixing the solution of the micronutrient balancers obtained with the third mixture at an addition rate of 0.2 ml/min with stirring to form the booster composition; and
    making up a final volume of the booster composition to one litre using 10% formic acid.

4. The method as claimed in claim 1, wherein preparing the booster composition comprises:
    preparing a solution of controlled release agents, a solution of redox potential balancers, a solution of direct interspecies electron transfer (DIET) improvers, a solution of micronutrient balancers, and a solution of co-factors, wherein each solution is prepared in 10% formic acid as a base medium;
    mixing the solution of the DIET improvers with the solution of the controlled release agents at an addition rate of 2.5 ml/min with continuous stirring to form a first mixture;
    mixing the solution of the co-factors with the first mixture at an addition rate of 0.6 ml/min with continuous stirring to form a second mixture;
    mixing the solution of the redox potential balancers with the second mixture at an addition rate of 5 ml/min with stirring to form a third mixture;
    mixing the solution of the micronutrient balancers obtained with the third mixture at an addition rate of 0.2 ml/min with stirring to form the booster composition; and
    making up a final volume of the booster composition to one litre using 10% formic acid.

5. The method as claimed in claim 1, wherein the digester is a covered anaerobic lagoon digester, a plug flow digester, a complete mix digester, a dry digester, or a continuous stirred tank reactor (CSTR) based digester.

6. The method as claimed in claim 5, wherein dosing the booster composition to the digester comprises dosing at a temperature in a range of 5-80° C.

7. The method as claimed in claim 1, wherein dosing the digester with the booster composition comprises dosing 25-100 ml of the booster composition per ton of organic waste.

8. The method as claimed in claim 1, wherein the booster composition is characterized to enable hydrolysis, acidogenesis, acetogenesis, and methanogenesis in the digester.

9. The method as claimed in claim 1, wherein dosing the booster composition comprises dosing in one staged, two staged, or multistage biomethanation plant.

10. The method as claimed in claim 1, wherein dosing the booster composition comprises dosing the booster composition continuously to the digester.

11. The method as claimed in claim 1, wherein dosing the booster composition comprises dosing the booster composition intermittently to the digester.

12. The method as claimed in claim 1, wherein dosing the booster composition comprises dosing the booster composition to the digester having 1-10 CFU/ml living cells.

13. The method as claimed in claim 1, wherein adding the biomethanation inoculum comprises adding 10% (v/v) of the biomethanation inoculum for carrying out biomethanation.

14. The method as claimed in claim 1, wherein adding the biomethanation inoculum comprises adding *Brevibacterium* sp. MTCC 25255; *Clostridium* sp. MTCC 25264; *Methanobacterium* sp. MTCC 25266; *Methanothermobacter* sp. MTCC 25268; *Methanosarcina* sp. MTCC 25300; *Desulfovibrio* sp. MTCC 25301; *Methanolobus* sp. MTCC 25302; *Methanosaeta* sp. MTCC 25303; *Thermotoga* sp. MTCC 25304; *Pyrococcus* sp. MTCC 25305; *Shewanella* sp. MTCC 25020, *Moorella* sp. MTCC 25267, *Lactobacillus* sp. MTCC 25282 or a microbial blend thereof.

15. The method as claimed in claim 1, wherein the biomethanation inoculum is grown anaerobically at 37° C. for 7 days.

16. The method as claimed in claim 1, wherein the organic waste comprises kitchen waste, paddy straw, press mud, cattle dung, municipal sewage waste (MSW).

17. The method as claimed in claim 4, further comprising storing the booster composition at a temperature of 4° C.

18. The booster composition as claimed in claim 1, comprising 10810-13512 ppm of controlled release agents, 75500-88000 ppm of redox potential balancers, 5750-8200 ppm of direct interspecies electron transfer (DIET) improvers, 6825-8232 ppm of micronutrient balancers, and 167-260 ppm of co-factors.

* * * * *